US005687075A

United States Patent [19]

Stothers

[11] Patent Number: 5,687,075

[45] Date of Patent: Nov. 11, 1997

[54] ADAPTIVE CONTROL SYSTEM

[75] Inventor: Ian MacGregor Stothers, Nr. Thethford, United Kingdom

[73] Assignee: Lotus Cars Limited, United Kingdom

[21] Appl. No.: 416,764

[22] PCT Filed: Oct. 21, 1993

[86] PCT No.: PCT/GB93/02170

§ 371 Date: Jun. 2, 1995

§ 102(e) Date: Jun. 2, 1995

[87] PCT Pub. No.: WO94/09481

PCT Pub. Date: Apr. 28, 1994

[30] Foreign Application Priority Data

Oct. 21, 1992 [GB] United Kingdom .................... 9222104

[51] Int. Cl.[6] .......................... G05B 13/02; A61F 11/06; H03B 29/00

[52] U.S. Cl. ................................ 364/148; 381/71; 381/94

[58] Field of Search .............................. 364/148; 381/71, 381/94

[56] References Cited

U.S. PATENT DOCUMENTS 4,238,746 12/1980 McCool et al. .......................... 333/166
5,170,433 12/1992 Elliot et al. ............................... 381/47
5,396,414 3/1995 Alcone .................................... 364/148
5,426,704 6/1995 Tamamura et al. ........................ 381/71
5,473,555 12/1995 Potter .................................. 364/724.1

FOREIGN PATENT DOCUMENTS 0 043 565 A1 7/1981 European Pat. Off. .
0 361 968 A2 9/1989 European Pat. Off. .
0 455 479 A3 5/1991 European Pat. Off. .
2 107 960 10/1982 United Kingdom .

OTHER PUBLICATIONS

"Active Control of Sound", *Academic Press*, London, U.K., 1992, By P.A. Nelson and S.J. Elliott, pp. 113–115.

*Primary Examiner*—Reba I. Elmore
*Assistant Examiner*—Robert J. Dolan
*Attorney, Agent, or Firm*—Westman, Champlin & Kelly, P.A.

[57] ABSTRACT

An adaptive control system for reducing undesired signals comprises sensors (31) to provide signals indicative of the undesired signals, and a processor (36) which processes the first signal to provide a secondary signal for output to sources (37) to interfere with the undesired signals. Sensors (42) are provided to detect the residual signals which are indicative of the interference between the undesired and secondary signals. Within the processor the signals indicative of the undesired signals and the residual signals are transformed into the frequency domain and collated. The outcome of the collation is inverse transformed and the processor adjusts the secondary signal using this inverse transform to reduce the residual signal from the sensors (42).

40 Claims, 5 Drawing Sheets

ADAPTIVE CONTROL SYSTEM

BACKGROUND OF THE INVENTION

The present invention relates to an adaptive control system and method for reducing undesired primary signals generated by a primary source of signals.

The basic principle of adaptive control is to monitor the primary signals and produce a cancelling signal which interfers destructively with the primary signals in order to reduce them. The degree of success in cancelling the primary signals is measured to adapt the cancelling signal to increase the reduction in the undesired primary signals.

This idea is thus applicable to any signals such as electrical signals within an electrical circuit in which undesired noise is produced. One particular area which uses such adaptive control is in the reduction of unwanted acoustic vibrations in a region.

It is to be understood that the term "acoustic vibration" applies to any acoustic vibration including sound.

There has been much work performed in this area with a view to providing a control system which can adapt quickly to changes in amplitude and frequency of vibrations from a source. Prior art adaptive control systems either operate in the time or frequency domain on the drive signal to be output to cancel the noise. A time domain system is disclosed in WO88/02912. In this document a controller is disclosed which is implemented as a digital adaptive finite impulse response (FIR) filter. In order for the filter to be adapted the filter coefficents must be modified based on the degree of success in cancelling the undesired vibrations. For such a control system disclosed in this document, where there are a large number of error signals, drive signals and reference signals, there are a large number of calculations which must be performed for each update of the coefficients. For instance, an estimate of the response of each sensor to each drive signal (the C filter) must be taken into consideration in the calculation of the update of the filter coefficients.

WO88/02912 also discloses the operation of a digital filter in the frequency domain. Such a filter has complex filter coefficients and requires the reference signal and error signals to be transformed into the frequency domain and the output drive signal from the adaptive filter to be inverse transformed back to the time domain in order to provide the drive signal. The transform which is conveniently used is the Fourier transform. In order for such a transform to be performed a number of data points within a window length are transformed and used to adapt the following window of data. Such a discrete Fourier transform provides good control if the length of the window (or number of data points) is long, but this provides a long delay in the update. A short window of data on the other hand provides for a quick adaption but poor control.

SUMMARY OF THE INVENTION

It is an object of the present invention to provide an adaptive control system which is computationally efficient compared with time domain adaptive control systems and which overcomes the problems associated with frequency domain adaptive control systems.

The present invention provides an adaptive control system for reducing undesired signals, comprising signal means to provide at least one first signal indicative of at least selected undesired signals; processing means adapted to use said at least one first signal to provide at least one secondary signal to interfere with the undesired signals; and residual means to provide for said processing means at least one residual signal indicative of the interference between said undesired and secondary signals; wherein said processing means is adapted to transform said at least one first signal and said at least one residual signal to provide the amplitude and phase of spectral components of said signals, to collate the transformed signals, to inverse transform of the outcome of said collation, and to adjust the or each secondary signal using the inverse transform of the outcome of the collation to reduce said at least one residual signal.

Preferably said processing means comprises adaptive response filter means having filter coefficients and adapted to adjust the or each-secondary signal using said filter coefficients to reduce the or each residual signals, and to modify the filter coefficients using said inverse transform of the outcome of the collation.

Also preferably said processing means is adapted to collate said transformed signals by forming at least one cross spectral estimate, to inverse transform said at least one cross spectral estimate, to form at least one cross correlation estimate and to modify the filter coefficients of said adaptive response filter using said at least one cross correlation estimate.

Preferably the processing means is adapted to digitally sample said at least one first signal and said at least one residual signal, and to store a plurality of digits for each said signal to form first signal data blocks and residual signal data blocks respectively, said first signal data blocks and said residual signal data blocks being time aligned; said processing means being further adapted to set a number of said digits at the end of each first signal data block to zero to form a modified first signal data block, and to transform the modified first signal data block and the associated residual signal data block to use in the collation.

Preferably the number of digits at the end of each modified first signal data block which is set to zero depend on the delay between the first signal and the contribution from the first signal in the residual signal. The number of digits set to zero are preferably selected such that the time taken to sample said number is greater than the delay experienced by a signal passing through said adaptive response filter.

Preferably the cross spectral estimate is formed by multiplying the complex conjugate of the transform of the first signal with the transform of the residual signal.

Preferably the transform performed on the first signal and the residual signal is the Fourier transform although any transform could be used in which the cross talk between frequencies is minimal or non-existent.

In order to control the stability of the adaptive control, preferably the cross spectral estimate is multiplied with a convergence coefficient which is sufficiently small to smooth out the effect of random errors in the cross spectral estimate on the adaption. Alternatively the cross correlation estimate is multiplied with a convergence coefficient sufficiently small to smooth out the effect of random errors in the cross correlation estimate on the adaption.

In one embodiment of the present invention the processing means includes system response filter means to model the response of the signals from said residual means to at least one secondary signal. In this embodiment said system response filter means preferably comprises complex filter coefficients which are an estimate of the frequency response of said residual signals to at least one said secondary signals, and said processing means is adapted to filter the transform of said at least one first signal using said complex filter coefficients.

In an alternative embodiment of the present invention the processing means includes system response filter means which comprises complex filter coefficients which are an estimate of the amplitude and an estimate of the inverse of the phase of the frequency response of said residual signals to at least one secondary signal, and said processing means is adapted to filter the transform of said at least one residual signal using said complex filter coefficients.

In another embodiment of the present invention the processing means is adapted to modify said filter coefficients to reduce the amplitude of portions of the or each drive signal by a predetermined amount. This action on the filter coefficients can be termed "effort weighting" and is used to control the stability of the adaptive response filter.

Preferably said residual means provides a plurality of residual signals and said processing means is adapted to modify said filter coefficients of said adaptive response filter to reduce the sum of the mean of the square of the residual signals.

In one embodiment wherein said undesired signals comprise undesired acoustic vibrations, said adaptive control system comprises at least one secondary vibration source responsive to said at least one secondary signal to provide secondary vibrations to interfere with said undesired acoustic vibrations; said residual means comprising at least one sensor means to sense the residual vibrations resulting from the interference between said undesired acoustic vibrations and said secondary vibrations and to provide said at least one residual signal.

The present invention also provides a method of actively reducing undesired signals, comprising the steps of providing at least one signal indicative of at least selected undesired signals using said at least one first signal to provide at least one secondary signal to interfere with said undesired signals; providing at least one residual signal indicative of the interference between said undesired and secondary signals; transforming said at least one first signal and said at least one residual signal to provide the amplitude and phase of spectral components of said signals, collating the transformed signals; inverse transforming the outcome of the collation and using the inverse transform of the output of the collation to adapt the or each secondary signal to reduce the residual signals.

In another aspect the present invention provides an adaptive control system for reducing undesired signals, comprising signal means to provide at least one first signal indicative of at least selected undesired signals; processing means adapted to use said at least one first signal to provide at least one secondary signal to interfere with the undesired signals; and residual means to provide for said processing means at least one residual signal indicative of the interference between said undesired and secondary signals; wherein said processing means is adapted to digitally sample said at least one first signal and said at least one residual signal; to store a plurality of digits for each said signal to form first signal and residual signal data blocks respectively, said first signal data blocks and said residual signal data blocks being time aligned; to set a number of said digits at the end of each first signal data block to zero to form a modified first signal data block, to transform the modified first signal data block and the residual signal data block to provide the amplitude and phase of spectral components of said signals, and to adjust the amplitude and phase of spectral components of said at least one secondary signal using said transformed signals to reduce said at least one residual signal.

In a further aspect the present invention provides a method of actively reducing undesired signals comprising the steps of providing at least one first signal indicative of at least selected undesired signals; using said at least one first signal to provide at least one secondary signal to interfere with said undesired signals; providing at least one residual signal indicative of the interference between said undesired and secondary signals; digitally sampling said at least one first signal and said at least one residual signal; storing a plurality of digits for each said signal to form first signal and residual signal data blocks, said first signal and residual signal data blocks being time aligned; setting a number of said digits at the end of each first signal data block to zero to form a modified first signal data block, transforming the modified first signal data block to provide the amplitude and phase of spectral components of said signals, and adjusting the amplitude and phase of spectral components of said at least one secondary signal using said transformed signals to reduce said at least one residual signal.

BRIEF DESCRIPTION OF THE DRAWINGS

Examples of the present invention will now be described with reference to the drawings, in which:

Referring now to the drawings, 1*a* and 1*b* illustrate alternative adaptive control systems which can be used in accordance with the present invention. Both FIGS. 1*a* and 1*b* illustrate a single channel system having a single reference signal x(n) which represents the signal from a sensor, and a single output y(n) from the w filter which represents the drive signal to a secondary vibration source. e(n) represents the error signal indicative of the residual vibrations after interference between the primary and secondary vibrations. The single channel system is shown for simplicity although the present invention is equally applicable to the multichannel system where the Fourier transform of each reference signal x(n) must be taken as well as the Fourier transform of each error signal e(n).

In FIGS. 1*a* and 1*b*, A represents the acoustic response of the pathway from the primary source of vibrations (represented by the reference signal x(n)) and the location of interference with the drive signal (y(n) from the adaptive filter w). The reference signal x(n) is input into the adaptive response filter w and this signal is modified by filter coefficients of the w filter to provide the drive signal y(n). In order to compensate for the acoustic response of the sensor to the output of the secondary vibration source (termed C) in the conventional time domain adaptive control system an estimate of C is used to modify the reference signal x(n) before it is input into the LMS algorithm. The C coefficients provide a model of the delay and reverberant response of the system. For a multichannel system with m secondary vibration sources and l sensors, the coefficients of the adaptive response filter w should be adjusted at every sample in the time domain according to the following equation:

$$\underline{w}_{mi}(n+1)=\underline{w}_{mi}(n)+\mu\sum_{l=1}^{L}e_l(n)r_{lm}(n-i)$$

where

μ is a convergence coefficient $e_l(n)$ is the sampled output from the $l^{th}$ sensor $r_{lm}(n)$ is a sequence formed by filtering the reference signal x(n) by C which models the response of the $l^{th}$ sensor to the output of the $m^{th}$ secondary vibration source.

This requires each reference signal to be filtered by a filter which has coefficients for all the paths between the secondary vibrations sources and the sensors.

Figure 1A:
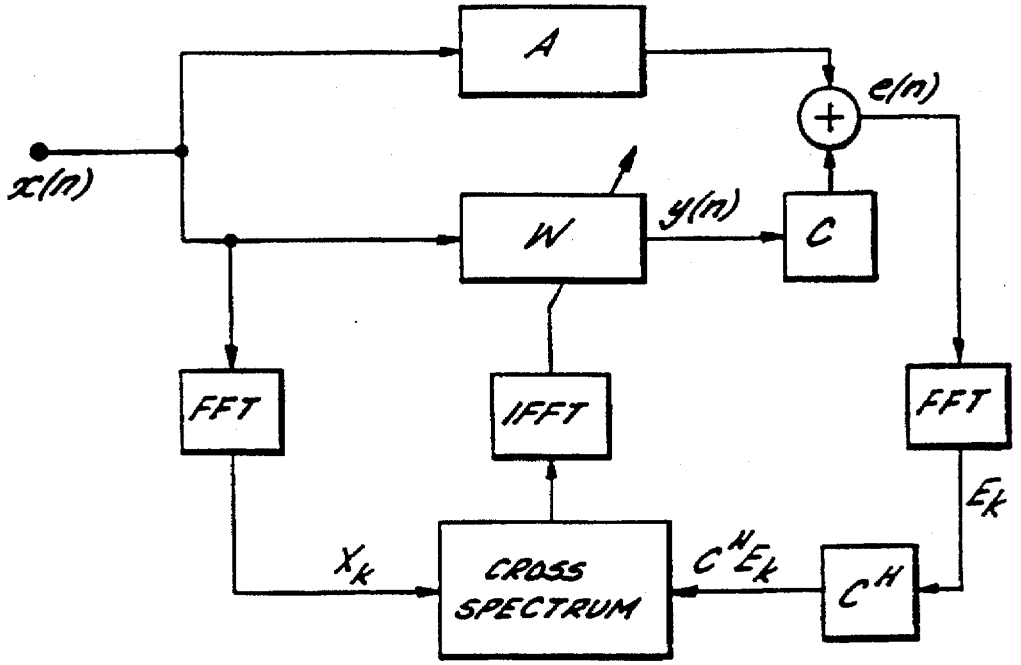
FIGS. 1*a* and 1*b* illustrate schematically alternative adaptive control systems according to embodiments of the present invention.
Figure 1B:
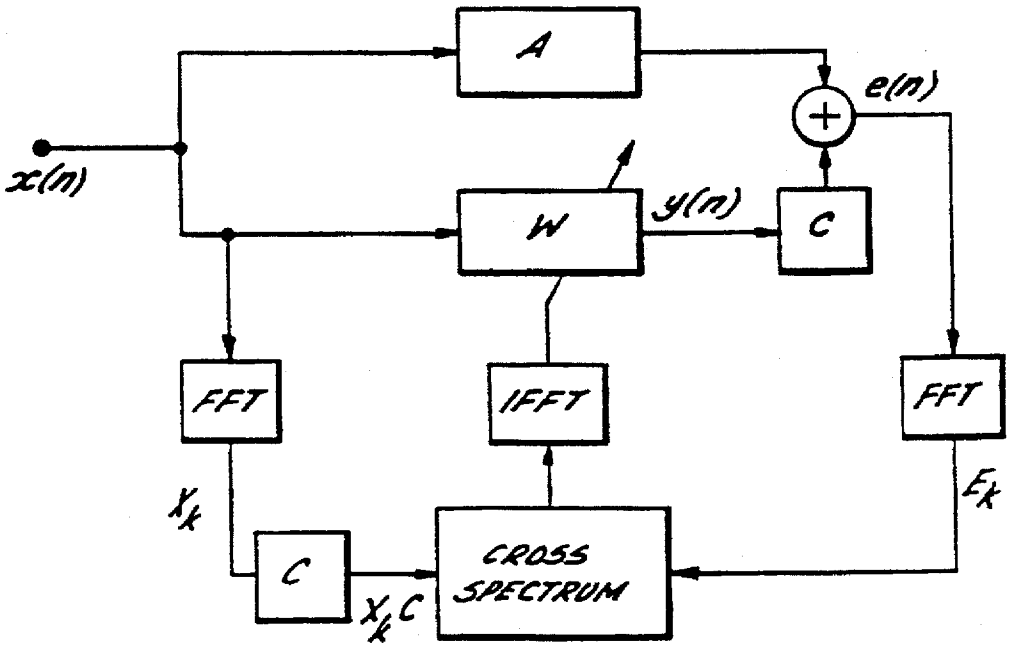

In the single channel embodiment shown in FIGS. 1*a* and 1*b*, the update required for the w coefficients is determined in the frequency domain and implemented in the time domain. This is achieved by taking the Fourier transform of the reference signal x(n) and the error signal e(n). The Fourier transform of the error signal $E_k$ is then convolved with the complex conjugate of the Fourier transform of the reference signal $X_k$ to form a cross spectral estimate. The inverse Fourier transform of this cross spectral estimate is then taken to form a cross correlation estimate. The causal part of the cross correlation estimate is then used to update the coefficients of the adaptive response filter w.

In the above no consideration has been given to compensating for the response of the sensors to the secondary vibration sources. FIGS. 1*a* and 1*b* show alternative methods for doing this. In FIG. 1*a* the Fourier transform $E_k$ of the error signal e(n) is multiplied by the complex conjugate of an estimate of the complex transfer function C for the $k^{th}$ iteration. The result of this operation is then multiplied by the complex conjugate of the Fourier transform of the reference signal $X_k$ to form the cross spectral estimate. Thus the update algorithm for the adaptive control system shown in FIG. 1*a* can be given by the following equation:

$$w(n+1)=w(n)-\mu IFFT[X^H{}_k(C^H E_k)]$$

where

μ is a convergence coefficient, $X_k$ represents a vector of complex values of the Fourier transform of the reference signal x(n) at the $k^{th}$ iteration $E_k$ represents a matrix of complex values of the Fourier transform of the error signals e(n) at the $k^{th}$ iteration C represents the matrix of transfer functions H denotes the complex conjugate of the matrix IFFT denotes the inverse fast Fourier transform of the term in the brackets.

The convergence coefficient is provided to increase the stability of the adaptive control system and it is sufficiently small to smooth out the effect of random errors in the cross spectral estimate on the adaption. Although in the above algorithm the convergence coefficient is multiplied by the cross correlation estimate, the convergence coefficient may equally be multiplied by the cross spectral estimate and the algorithm is given by:

$$w(n+1)=w(n)-IFFT[\mu X^H{}_k(C^H E_k)]$$

In the above equations the C matrix contains the transfer functions or a model of the amplitude and phase change applied to each drive signal as detected by each sensor, whereas the conjugate of the C matrix represents a model of the amplitude and the inverse of the phase.

Thus in the active vibration control system illustrated in FIG. 1*a* there are three Fourier transform operations to be undertaken for the update data and the transform $E_k$ of each error signal must be multiplied by the conjugate of the transfer functions C for each path from a secondary vibration source to an error sensor. The time taken for the calculations in the arrangement shown in FIG. 1*a* are approximately proportional to $(\log_2 N\times N)\times$(No. of error sensors×No. of secondary vibration sources). If this is compared with the computational time of the conventional time domain algorithm which is approximately proportional to $N^2\times$(No. of references×No. of error sensors×No. of secondary vibration sources), it can be seen that even for a single channel system the control system shown in FIG. 1*a* is more computationally efficient for an adaptive response filter w having a number of taps of about 64 or greater. The computation of the cross correlation estimate by firstly calculating the cross spectral estimate reduces the number of calculation steps required since the formation of the cross correlation estimate in the time domain requires the convolving of the reference and error signals, whereas in the frequency domain the formation of the cross spectral estimate can be achieved merely by multiplying the functions.

Where advantages of the control system of FIG. 1 are fully utilised is in a multichannel system where a number of reference signals, a number of secondary vibration sources and a number of error sensors are provided. For the control system shown in FIG. 1*a*, each of the reference signals does not have to be filtered by a model of the sensor responses to the secondary vibration sources. This reduction in computation is in addition to the computational saving discussed above for the single channel system.

FIG. 1*b* illustrates an alternative active vibration control system according to one embodiment of the present invention. In this arrangement the only difference is in the position of the estimate of C. Instead of multiplying the Fourier transform of the error signal by the complex conjugate of C, the Fourier transform of the reference signal is multiplied by the matrix of transfer functions C. The cross spectral estimate is then formed by taking the complex conjugate of the result of passing the Fourier transform of the reference signal through the C filter and multiplying this complex conjugate with the Fourier transform of the error signal. The algorithm is given by:

$$w(n+1)=w(n)-IFFT[(CX_k)^H E_k]$$

As for the arrangement shown in FIG. 1*a*, the cross correlation estimate is multiplied by a convergence coefficient μ in order to compensate for random errors. In a like manner to that shown in FIG. 1*a* the cross spectral estimate can alternatively be multiplied with the convergence coefficient and then the algorithm is given by:

$$w(n+1)=w(n)-IFFT[(CX_k)^H E_k]$$

For the arrangement shown in FIG. 1*b*, the computational efficiency for the single channel system is the same as that of the arrangement shown in FIG. 1*a*. This control system also benefits from forming the cross correlation estimate by firstly forming the cross spectral estimate. When there is a single reference signal and a number of secondary vibration sources and error sensors, the arrangement shown in FIG. 1*b* is equally as computationally efficient as the arrangement shown in FIG. 1*a*. However, when more than one reference signal is used the computational efficiency of the arrangement shown in 1*b* compared to the arrangement shown in FIG. 1*a* decreases since it is approximately proportional to ($\log_2$N×N)×(No. of references×No. of error sensors×No. of secondary vibration sources). The number of filtering operations that must be carried out by the transfer function C is increased by a factor which is the number of reference signals.

Figure 1C:
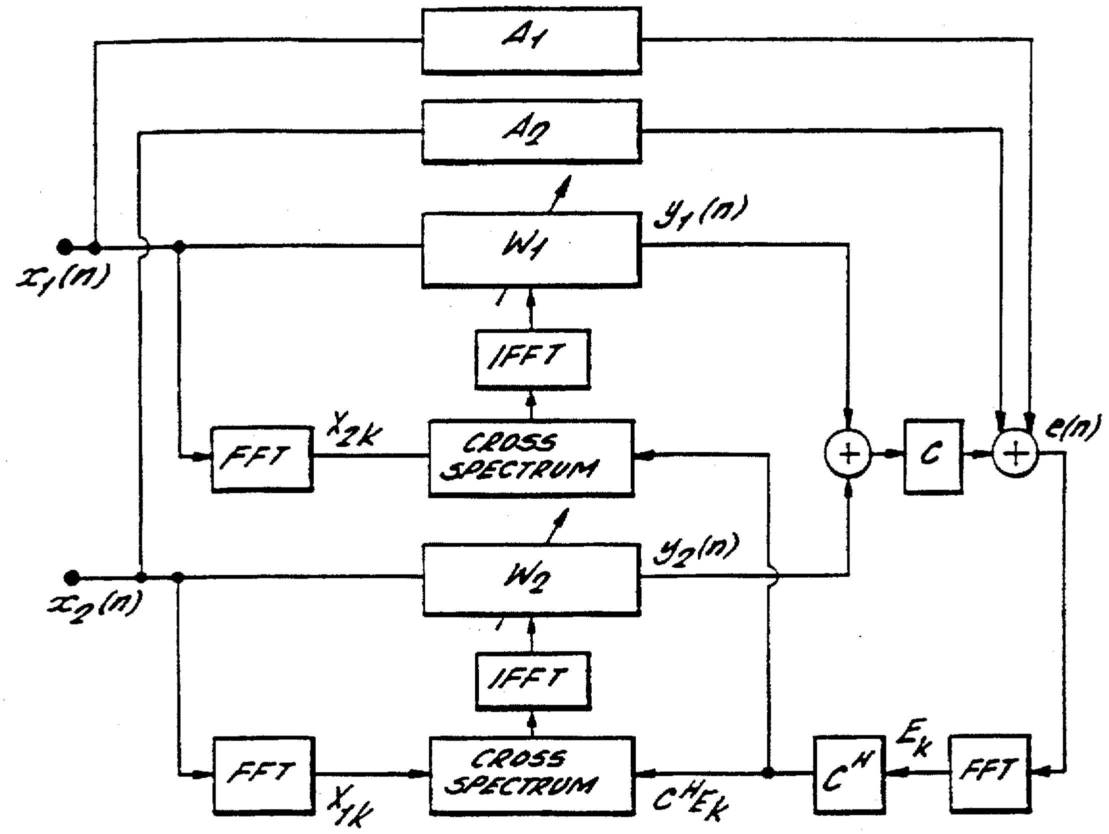
FIG. 1*c* illustrates an expansion of the arrangement shown in FIG. 1*a* for two reference signals.
Figure 1D:
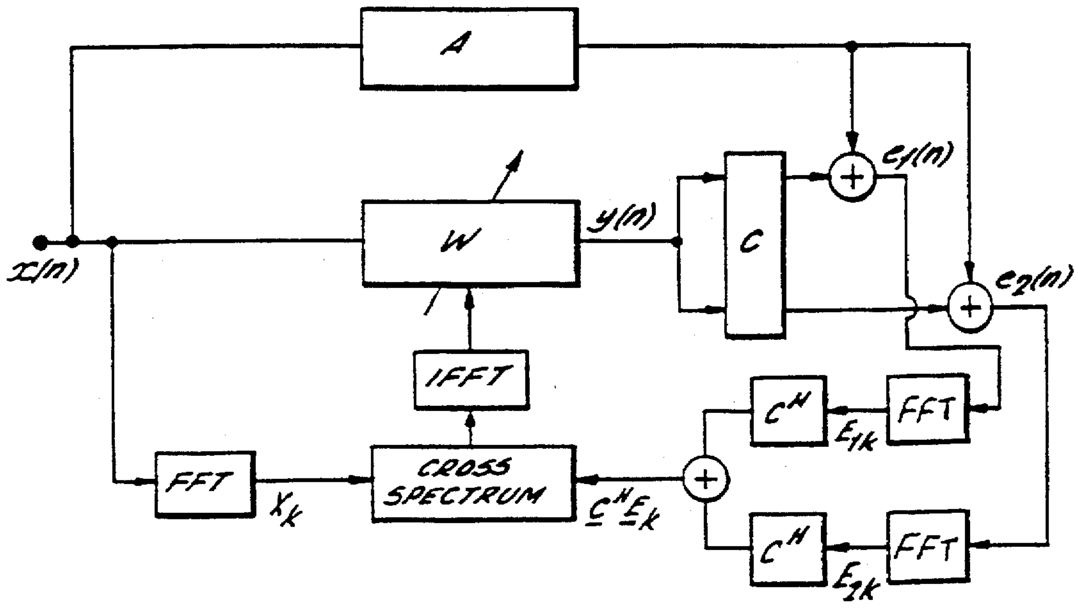
FIG. 1*d* illustrates an expansion of the arrangement shown in FIG. 1*a* for two error sensors.
Figure 1E:
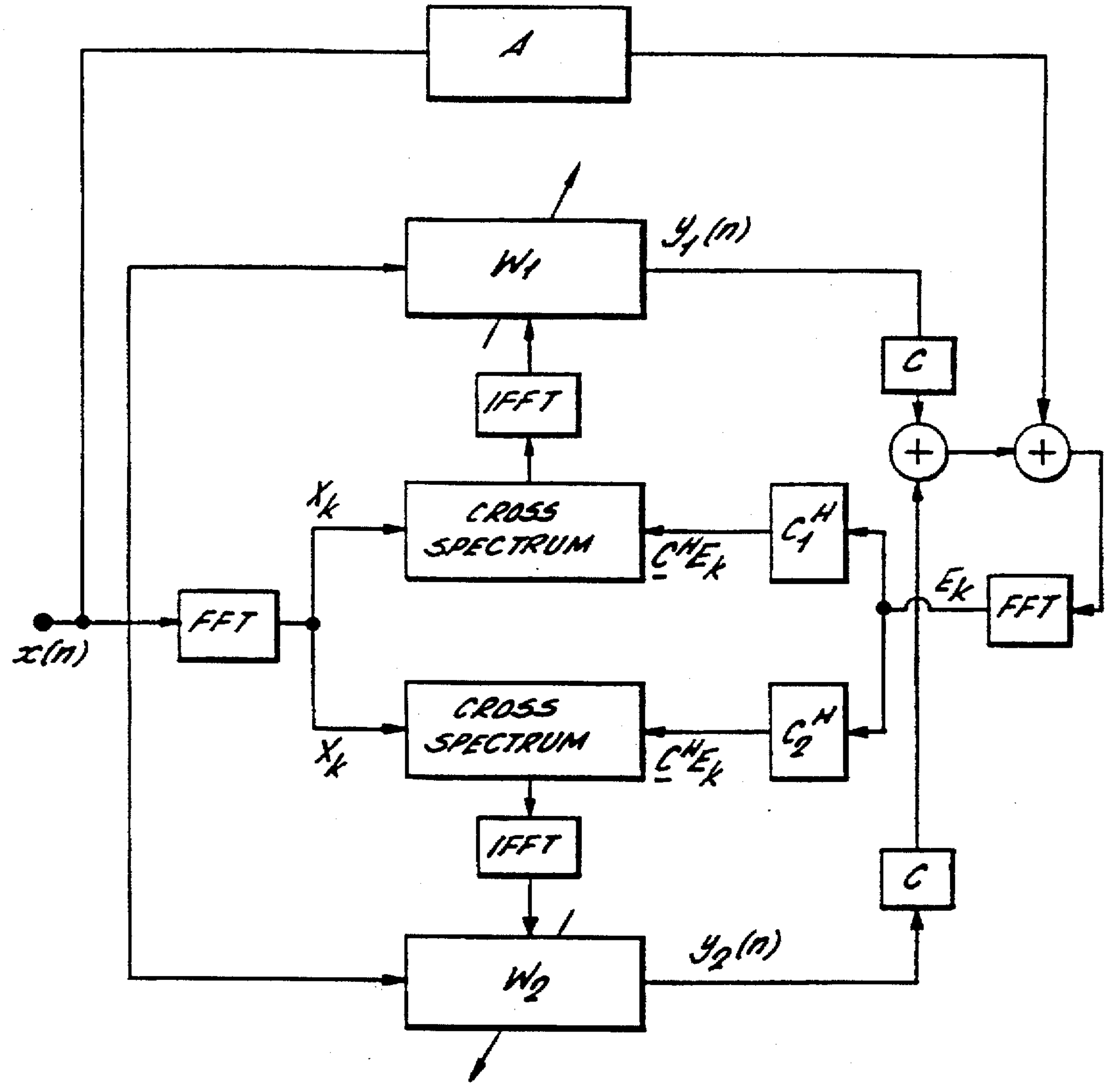
FIG. 1*e* illustrates an expansion of the arrangement shown in FIG. 1*a* for two secondary vibration sources.

FIGS. 1*c*, 1*d* and 1*e* illustrate three control systems with 1) two reference signals, one secondary vibration source and one error sensor, 2) one reference signal, one secondary vibration source and two error sensors, and 3) one reference signal, two secondary vibration sources and one error sensor.

These three drawings illustrate how a multichannel system with a number of references, secondary vibration sources and error sensors provide a complex system with a matrix C of transfer functions, a number of Fourier transformed reference signals $X_k$, and a number of Fourier transformed error signals $E_k$. The arrangements shown in FIGS. 1*c*, *d* and *e* are multichannel versions of the single channel system shown in FIG. 1*a*. A multichannel system of the model shown in FIG. 1*b* can be built up in a like manner to that shown in FIGS. 1*c*, *d* and *e* as would be evident to a skilled person in the art.

In the multichannel system with a number of error sensors the algorithm reduces the noise by reducing the sum of the mean of the square of the error signals in a similar manner to that disclosed in WO88/02912.

In addition to the modification of the filter coefficients to reduce the sum of the mean of the square of the error signals, the filter coefficients can be modified to reduce the amplitude of portions of the drive signals by a predetermined amount. This is termed "effort weighting" and can increase the stability of the algorithm as well as allow for selection of the effort taken to converge for signals of different delays or different frequencies dependent upon whether the filter coefficients are weighted in the time or frequency domain.

So far in considering the way in which the algorithm works, no consideration has been given to the practical considerations of taking the Fourier transform of the continuous reference signal x(n) and error signal e(n). In order to perform a discrete fast Fourier transform a block or window of data must be stored and operated on. The number of data points which are required must at least correspond to the delay associated with the adaptive response filter w since for a reference signal x(n) the effect on it by the w filter presented in the error signal e(n) must be present.

If the block of reference data has a number n of data points for operation on by the Fourier transform then the $n^{th}$ data point will have a contribution in the error signal e(n) which is delayed by the length of the w filter. Thus if a time aligned window of error data e(n) was taken, the delayed contributions from the $n^{th}$ data point in the reference signal would not be measured. This reduces the possibility of convergence of the algorithm. This problem is overcome by taking a block or window of data having n data points where the last few p data points are set to zero. Thus the block of data has a length of 0 to n but only the data points 0 to n–p contain actual reference signal data. The number p of data points which are set to zero is dependent on the number of tap delays of the w filter. The number p should be set to be at least the same number if not greater than the number of taps in the w filter.

Figure 2:
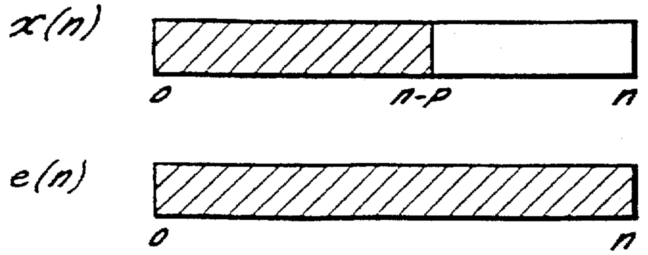
FIG. 2 illustrates the blocks of reference and error signal data used for the transform to form the cross spectral estimate.

Using this method assures that all contributions from the reference signal data point x(n–p) are contained within the error signal data block e(n) for the two time aligned blocks of data. FIG. 2 illustrates the two data blocks for the reference and error signals. These blocks of data are used for the fast Fourier transform and this method ensures that all contributions from the reference signal data points are found in the error signal data block.

The data blocks or windows represent "snap shots" in time of the reference and error signals. There is no requirement for these data blocks to be taken end to end. Blocks of data can be taken at intervals of time. If the intervals between the acquisition of the data blocks is large then clearly the adaption of the coefficients of the w filter will be slow in response to rapidly changing conditions. However, for many practical applications the update of the coefficients of the w filter need not take place rapidly.

Thus because the adaption of the reference signal by the w filter coefficients takes place in the time domain, the output drive signals to provide the secondary vibrations are not delayed. Only the modification of the filter coefficients of the w filter are delayed.

Figure 3:
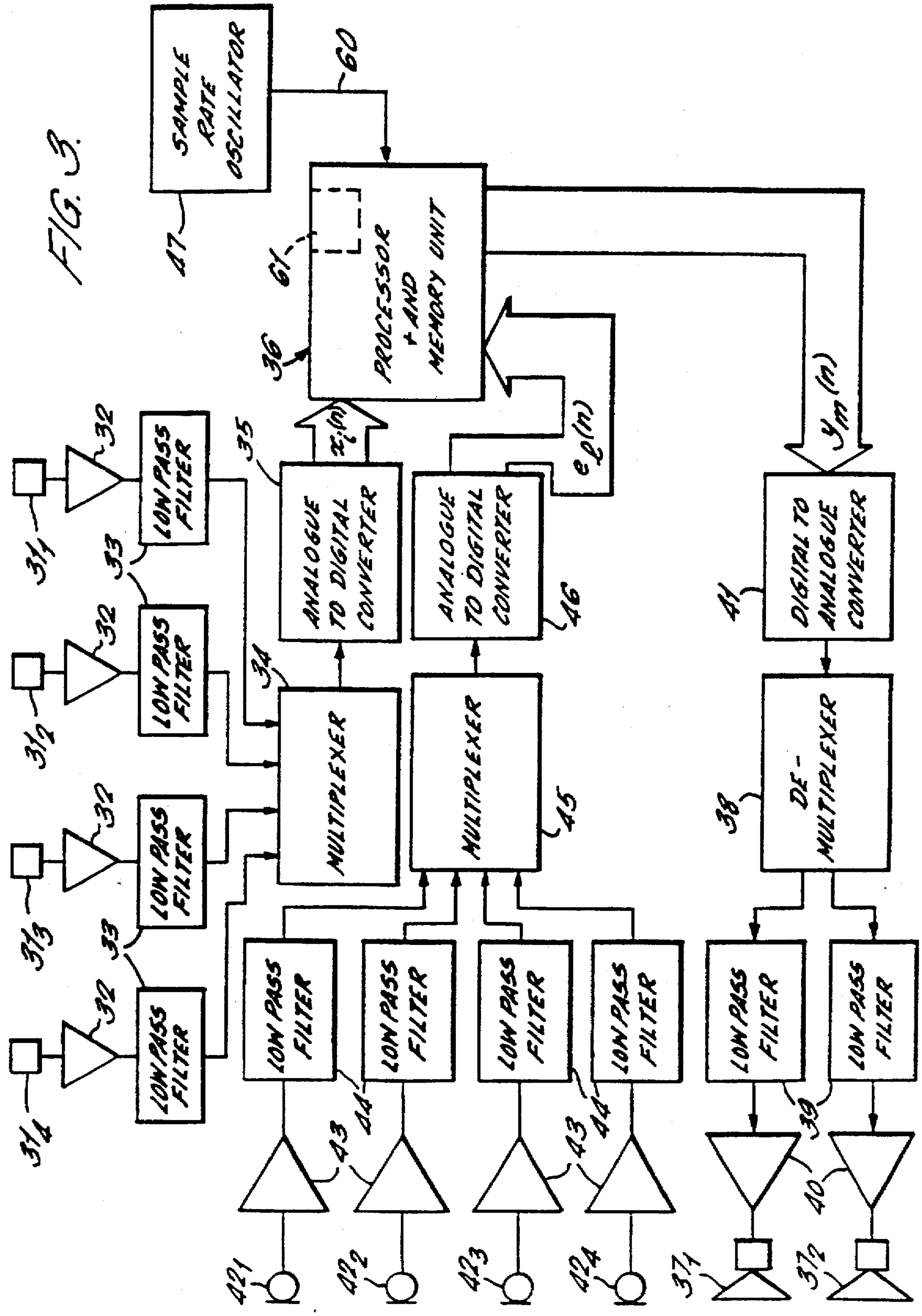
FIG. 3 is a schematic drawing of an active vibration control system for practical implementation.

So far only the method of operation of the algorithm has been considered. FIG. 3 illustrates the construction of a practical active vibration control system for use in a motor vehicle. FIG. 3 illustrates a multichannel system with four reference signal generators 31, four error sensors 42 and two secondary vibration sources 37. As mentioned hereinabove the present invention is particularly suited to a multichannel system having more than one reference signal since this provides for the greatest computational saving. In the arrangement shown in FIG. 3 the reference signal generators 31 comprise four transducers such as accelerometers placed on the suspension of the vehicle. These transducers provide signals indicative of the vibrational noise transmitted from the road wheel to the vehicle cabin. The outputs of the transducers 31 are amplified by the amplifiers 32 and low pass filtered by the filters 33 in order to avoid aliasing. The reference signals are then multiplexed by the multiplexer 34 and digitised using the analogue digital converter 35. This provides reference signals $x_i(n)$ to the processor 36 which is provided with memory 61.

Four error sensors 42 are provided within the vehicle cabin at space locations such as around the headlining. These microphones $42_1$ through $42_4$ detect the noise within the cabin. The output of the microphones 42 is then amplified by the amplifiers 43 and low pass filtered by the low pass filters 44 in order to avoid aliasing. The output of the low pass filters 44 is then multiplexed by the multiplexer 45 before being digitised by the analogue to digital converter 46. The output of the analogue digital converter $e_l(n)$ is then input into the processor 36.

Drive signals $y_m(n)$ are output from the processor 36 and converted to an analogue signal by the digital to analogue converter 41. The output of the analogue to digital converter 41 is then demultiplexed by the demultiplexer 38. The demultiplexer 38 separates the drive signals into separate drive signals for passage through low pass filters 39 in order to remove high frequency digital sampling noise. The signal is then amplified by the amplifiers 40 and output to the secondary vibration sources $37_1$ and $37_2$ which comprise loudspeakers provided within the cabin of the vehicle. Conveniently, the loudspeakers can comprise the loudspeakers of the in-car entertainment system of the vehicle. In such an arrangement the drive signals are mixed with the in-car entertainment signals for output by the loudspeakers, as is disclosed in GB 2252657.

Thus the processor is provided with the reference signals $x_i(n)$ and the error signals $e_l(n)$ and outputs the drive signals $y_m(n)$ and is adapted to perform the algorithm as hereinbefore described.

Although in FIG. 3 the analogue to digital converters 35 and 46 and the digital to analogue converter 41 are shown separately, such can be provided by a single chip. FIG. 3 also shows the processor receiving a clock signal 60 from a sample rate oscillator 47. The processor thus operates at a fixed frequency related to the frequencies of the vibrations to be reduced only by the requirement to meet Nyquist's criterion. The processor 36 can be a fixed point processor such as the TMS 320 C50 processor available from Texas Instruments. Alternatively, the floating point processor TMS 320 C30 also available from Texas Instruments can be used to perform the algorithm.

Although the arrangement shown in FIG. 3 illustrates a system for cancelling road noise transmitted from the road wheel of a vehicle, the system can also be used for cancelling engine noise where a reference signal is provided indicative of the noise generated by the engine of a vehicle. In this instance only a single-reference signal is required and although the full potential computational saving of the algorithm is not utilised, the computational requirement is still reduced compared to the conventional time domain algorithm.

Further, although the secondary vibration sources illustrated in FIG. 3 are loudspeakers they could alternatively be vibrators or a mix of both.

Figure 4A:
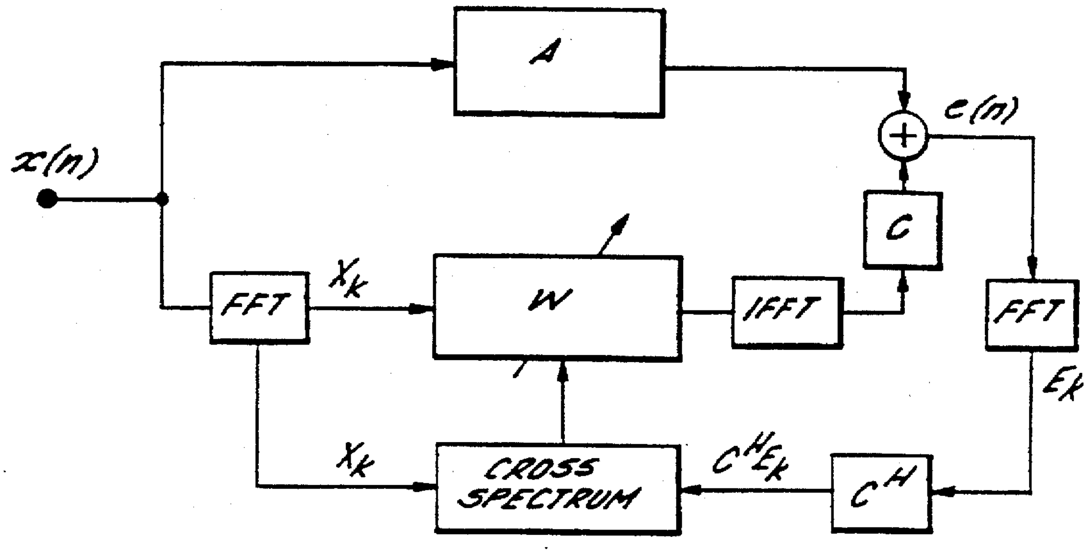
FIGS. 4*a* and 4*b* illustrate schematically frequency domain adaptive control systems in accordance with embodiments of the present invention.
Figure 4B:
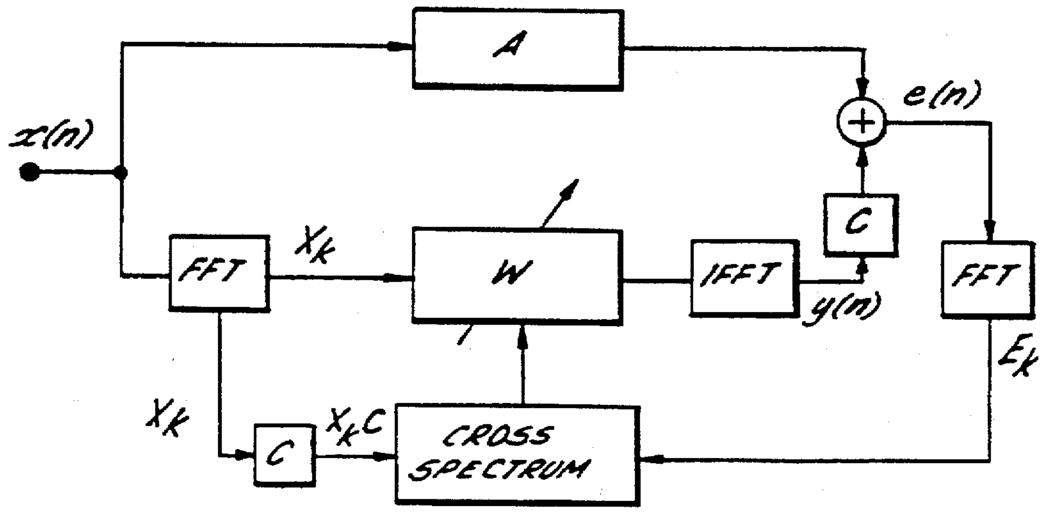

FIGS. 4*a* and 4*b* illustrate other embodiments of the present invention. In these embodiments adaption is performed in the frequency domain. FIGS. 4*a* and 4*b* differ from FIGS. 1*a* and 1*b* in that the w filter coefficients are complex and require the input to the w filter to be the transform of the reference signal. Also, there is no need to inverse transform the cross spectral estimate to modify the complex filter coefficients. The output of the w filter must be inverse transformed to generate the drive signal y(n) since the w filter acts on the amplitude and phase of spectral components.

For the arrangement in FIG. 4*a* the algorithm can be given by $$w_{k+1}=w_k-\mu X^H_k(C^H E_k)$$

whereas for FIG. 4*b* the algorithm can be given by $$w_{k+1}=w_k-\mu(CX_k)^H E_k$$

As for the arrangements shown in FIGS. 1*a* and 1*b* in order to avoid the problem of the window of error data not containing the contribution from the reference data in a time aligned window, the latter part of the error data block is zeroed in the manner described with respect to FIG. 2 with all the associated advantages.

Although the embodiments of the invention described hereinabove have been described with reference to an active vibration control system the present invention is not limited thereto. The present invention applies to the reduction of any undesired signals. A signal indicative of at least selected undesired vibrations from a vibration source is used to provide a drive signal to cancel the undesired vibrations at a location. The degree of success in reducing the undesired vibrations is measured to provide a residual signal and this is used to adjust the drive signal to provide better cancellation. Thus the undesired signals being cancelled could be electrical or acoustic.

I claim:

1. An adaptive control system for reducing undesired signals, comprising signal means to provide at least one first signal indicative of at least some of the undesired signals; processing means which processes said at least one first signal to provide at least one secondary signal to interfere with the undesired signals; and residual means to provide for said processing means at least one residual signal indicative of the interference between said undesired and secondary signals; wherein said processing means comprises: means for transforming said at least one first signal and said at least one residual signal to provide the amplitude and phase of spectral components of said signal; means for collating the transformed signals; means for inverse transforming of the outcome of said collation; adaptive response filter means having filter coefficients which filters the at least one first signal in providing the at least one secondary signal; means for adapting said filter coefficients to reduce each residual signal, which means for adapting adapts said filter coefficients using said inverse transform of the outcome of the collation; wherein: said means for collating said transformed signals has means for forming at least one cross spectral estimate; said means for inverse transforming of the outcome of the collation inverse transforms said at least one cross spectral estimate to form at least one cross correlation estimate; and said means for adapting the filter coefficients of said adaptive response filter means uses said at least one cross correlation estimate when adapting the filter coefficients.

2. An adaptive control system as claimed in claim 1 wherein said processing means comprises means for digitally sampling said at least one first signal and said at least one residual signal; means for storing a first plurality of digits for each signal which forms first signal and residual signal data blocks respectively; and means for time aligning said first signal data blocks and said residual signal data blocks; said processing means further comprising means for setting a second plurality of said digits at the end of each first signal data block to zero and thereby forming a modified first signal data block; and means for transforming the modified first signal data block and the time aligned residual signal data block to use in the collation.

3. An adaptive control system as claimed in claim 2, wherein said means for setting the second plurality of said digits at the end of each first signal data block to zero operates in dependence upon a delay between the first signal and the contribution from the first signal in the residual signal; and said processing means for setting a number of said digits at the end of each first signal data block to zero comprises means for selecting a number of digits to set to zero such that the time taken to sample said number is greater than the delay experienced by a signal passing through said adaptive response filter means.

4. An adaptive control system as claimed in claim 1, wherein said means for forming the cross spectral estimate has means for multiplying a complex conjugate of the transform of the first signal with the transform of the residual signal.

5. An adaptive control system as claimed in claim 1, wherein said processing means has means for multiplying said at least one cross spectral estimate with a convergence coefficient to reduce the effect of random errors in the cross spectral estimate on the filtering of the at least one first signal.

6. An adaptive control system as claimed in claim 1, wherein said processing means has means for multiplying said at least one cress correlation estimate with a convergence coefficient to reduce the effect of random errors in the cross correlation estimate on the filtering of the at least one first signal.

7. An adaptive control system as claimed in claim 1, wherein said processing means further includes system response filter means to model the response of said residual means to at least one secondary signal and said system response filter means comprises complex filter coefficients which represent the frequency response of said residual means to at least one said secondary signal, and said processing means has means for filtering the transform of said at least one first signal using said complex filter coefficients.

8. An adaptive control system as claimed in claim 1, wherein said processing means further includes system response filter means comprising complex filter coefficients which represent the amplitude and the inverse of the phase of the frequency response of said residual means to at least one said secondary signal, and said processing means has means for filtering the transform of said at least one residual signal using said complex filter coefficients.

9. An adaptive control system as claimed in claim 1, wherein said means for adapting said filter coefficients operates to reduce the amplitude of each secondary signal.

10. An adaptive control system as claimed in claim 1, wherein said residual means provides a plurality of residual signals; and said means for adapting said filter coefficients of said adaptive response filter operates to reduce the sum of the mean of the square of the residual signals.

11. An adaptive control system as claimed in claim 1, wherein: said undesired signals comprise undesired acoustic vibrations; said adaptive control system comprises at least one secondary vibration source responsive to said at least one secondary signal to provide secondary vibrations to interfere with said undesired acoustic vibrations; said residual means comprises at least one sensor means which senses the residual vibrations resulting from the interference between said undesired acoustic vibrations and said secondary vibrations and provides said at least one residual signal.

12. A method of actively reducing undesired signals comprising the steps of: providing at least one first signal indicative of at least some of the undesired signals; using said at least one first signal to provide at least one secondary signal to interfere with said undesired signals; providing at least one residual signal indicative of the interference between said undesired and secondary signals; transforming said at least one first signal and said at least one residual signal to provide the amplitude and phase of spectral components of said signals; collating the transformed signals; inverse transforming the outcome of the collation; filtering said at least one secondary signal using filter coefficients in an adaptive response filter means to reduce the residual signals; adapting the filter coefficients using said inverse transform of the outcome of the collation; wherein the transformed signals are collated by forming at least one cross spectral estimate; said at least one cross spectral estimate is inverse transformed to form at least one cross correlation estimate; and said means for adapting said filter coefficients uses said at least one cross correlation.

13. A method as claimed in claim 12, wherein said at least one first signal and said at least one residual signal are digitally sampled, including the steps of: storing in electronic memory means a first plurality of digits for each said signal to form first signal data blocks and residual signal data blocks respectively; time aligning said first signal data blocks and residual signal data blocks; setting a second plurality of said digits at the end of each first signal data block to zero to form a modified first signal data block; and transforming the modified first signal block and the time aligned residual signal data block for use in the collation.

14. A method as claimed in claim 13, wherein the second plurality of digits at the end of each modified first signal data block which is set to zero are selected in dependence upon the delay between the first signal and the contribution from the first signal in the residual signal, and the number of digits set to zero is determined to be at least the same number as the number of taps in the adaptive filter means such that the time taken to sample said number is greater than the delay experienced by a signal during filtering of the at least one first signal.

15. A method as claimed in claim 12, wherein the cross spectral estimate is formed by multiplying the complex conjugate of the transform of the first signal with the transform of the residual signal.

16. A method as claimed in claim 12, wherein the cross spectral estimate is multiplied with a convergence coefficient to reduce the effect of random errors in the cross spectral estimate on the filtering of the the at least one first signal.

17. A method as claimed in, claim 12, wherein the cross correlation estimate is multiplied with a convergence coefficient to reduce the effects of random errors in the cross correlation estimate on the filtering of the at least one first signal.

18. A method as claimed in claim 12, wherein the response of said at least one residual signal to said at least one secondary signal is modelled by system response filter means, and said system response filter means has complex filter coefficients which represent the frequency response of said at least one residual signal to at least one said secondary signal, said method including the steps of multiplying the said transform of said at least one first signal with said complex filter coefficients.

19. A method as claimed in claim 12, including the step of filtering the transform of said at least one residual signal using system response filter means which comprises complex filter coefficients which represent the amplitude and the inverse of the phase of the frequency response of said sensed residual vibration to said at least one secondary signal.

20. A method as claimed in claim 12, including the step of adapting said filter coefficients to reduce the amplitude of each secondary signal.

21. A method as claimed in claim 12, including the steps of using sensor means to sense residual signals in a plurality of locations to provide a plurality of residual signals and adapting said filter coefficients to reduce the sum of the square of the residual signals.

22. A method as claimed in claim 12, wherein said undesired signals comprise undesired acoustic vibrations, the method comprising the steps of: converting said at least one secondary signal into at least one secondary vibration using vibration means, the at least one secondary vibration interfering with said undesired vibrations: and using sensor means to sense the residual vibrations resulting from the interference between said undesired and secondary vibrations and to provide said residual signal.

23. An adaptive control system for reducing undesired signals, comprising signal means to provide at least one first signal indicative of at least some of the undesired signals; processing means which processes said at least one first signal to produce at least one secondary signal to interfere with the undesired signals; and residual means to provide for said processing means at least one residual signal indicative of the interference between said undesired and secondary signals; wherein said processing means comprises means for digitally sampling said at least one first signal and said at least one residual signal; means for storing a first plurality of digits for each said signal to form first signal and residual signal data blocks respectively; means for setting a second plurality of said digits at the end of each first signal data block to zero to form a modified first signal data block; means for transforming the modified first signal data block and the residual signal data block to provide the amplitude and phase of spectral components of said signals; means for transforming the at least one first signal to provide the amplitude and phase of spectral components of said signal; adaptive response filter means which filters the transformed first signal using complex filter coefficients in the provision of each secondary signal; and means for inverse transforming the filtered transformed first signal in the provision of said at least one secondary signal; wherein said processing means has means for forming at least one cross spectral estimate using the transforms of said at least one modified first signal data block and said at least one residual signal data block; and means for adapting the filter coefficients using said at least one cross spectral estimate.

24. An adaptive control system as claimed in claim 23, wherein said processing means has means for setting the second plurality of said digits at the end of each modified first signal data block to zero which operates in dependence upon a delay between the first signal and the contribution from the first signal in the residual signal, and has means for selecting the number of digits to set to zero such that the time taken to sample said number is greater than the delay experienced by a signal passing through said adaptive response filter means.

25. An adaptive control system as claimed in claim 23, wherein said means forming the cross spectral estimate multiplies a complex conjugate of the transform of the first signal with the transform of the residual signal.

26. An adaptive control system as claimed in claim 23, wherein said processing means has means for multiplying said at least one cross spectral estimate with a convergence coefficient to reduce the effect of random errors in the cross spectral estimate on the filtering of the at least one first signal.

27. An adaptive control system as claimed in claim 23, wherein said processing means further includes system response filter means to model the response of said residual means to at least one secondary signal and said system response filter means comprises complex filter coefficients which represent the frequency response of said residual means to at least one said secondary signal, and said system response filter means filters the transform of said at least one first signal using said complex filter coefficients.

28. An adaptive control system as claimed in claim 23, wherein said processing means further includes system response filter means comprising complex filter coefficients which represent the amplitude and the inverse of the phase of the frequency response of said residual means to at least one said secondary signal, and said system response filter means for filtering the transform of said at least one residual signal using said complex filter coefficients.

29. An adaptive control system as claimed in claim 23, wherein said means for adapting said filter coefficients reduces the amplitude of each secondary signal.

30. An adaptive control system as claimed in claim 23, wherein said residual means provides a plurality of residual signals, and said means for adapting said filter coefficients of said adaptive response filter reduces the sum of the mean of the square of the residual signals.

31. An adaptive control system as claimed in claim 23, wherein: said undesired signals comprise undesired acoustic vibrations; said adaptive control system comprises at least one secondary vibration source responsive to said at least one secondary signal to provide secondary vibrations to interfere with said undesired acoustic vibrations; said residual means comprises at least one sensor means which senses the residual vibrations resulting from the interference between said undesired acoustic vibrations and said secondary vibrations and which provides said at least one residual signal.

32. A method of actively reducing undesired signals comprising the steps of using sensor means to sense undesired signals and to provide at least one first signal indicative of at least some of the undesired signals; using said at least one first signal to provide at least one secondary signal to interfere with said undesired signals; using residual means to provide at least one residual signal indicative of the interference between said undesired and secondary signals; digitally sampling said at least one first signal and said at least one residual signal; storing a first plurality of digits for each said signal to form first signal and residual signal data blocks; time aligning said first signal and residual signal data blocks; setting a second plurality of said digits at the end of each first signal data block to zero to form a modified first signal data block; transforming the modified first signal data block to provide the amplitude and phase of spectral components of said signals; transforming the at least one first signal to provide the amplitude and phase of spectral components of said signal; filtering the transformed at least one first signal using complex filter coefficients in an adaptive response filter means; inverse transforming the filtered transform of the at least one first signal in provision of said at least one secondary signal; wherein at least one cross spectral estimate is formed using the transform of said at least one modified first signal data block and said at least one residual signal data block; and the complex filter coefficients are adapted using said at least one cross spectral estimate.

33. A method as claimed in claim 32, wherein the second plurality of digits at the end of each modified first signal data block which are set to zero are selected in dependence upon the delay between the first signal and the contribution from the first signal in the residual signal, the selection of digits set to zero being determined so that the number of digits set to zero is at least the same number as the number of taps in the adaptive filter means, such that the time taken to sample said number is greater than the delay experienced by a signal during adjustment of the or each secondary signal.

34. A method as claimed in claim 32, wherein the cross spectral estimate is formed by multiplying the complex conjugate of the transform of the first signal with the transform of the residual signal.

35. A method as claimed in claim 32, wherein the cross spectral estimate is multiplied with a convergence coefficient to reduce the effect of random errors in the cross spectral estimate on the filtering of the at least one first signal.

36. A method as claimed in claim 32, wherein the response of said at least one residual signal to said at least one secondary signal is modelled by system response filter means and said system response filter means has complex filter coefficients which represent the frequency response of said at least one residual signal to at least one said secondary signal, said method including the step of multiplying the said transform of said at least one first signal with said complex filter coefficients.

37. A method as claimed in claim 32, including the step of filtering the transform of said at least one residual signal using system response filter means which comprises complex filter coefficients which represent the amplitude and the inverse of the phase of the frequency response of said sensed residual vibration to said at least one secondary signal.

38. A method as claimed in claim 32, including the step of adapting said filter coefficients to reduce the amplitude of each secondary signal.

39. A method as claimed in claim 32, including the steps of using sensor means to sense residual signals in a plurality of locations to provide a plurality of residual signal and adapting said filter coefficients to reduce the sum of the square of the residual signals.

40. A method as claimed in claim 32, wherein said undesired signals comprise undesired acoustic vibrations, the method comprising the steps of converting said at least one secondary signal to at least one secondary vibration using vibration means, the at least one secondary vibration interfering with said undesired vibrations, and sensing the residual vibrations resulting from the interference between said undesired and secondary vibrations to provide said residual signal.

* * * * *